United States Patent [19]

Holzermer

[11] Patent Number: 4,514,859
[45] Date of Patent: Apr. 30, 1985

[54] COLLIMATOR FOR AN X-RAY EXAMINATION APPARATUS

[75] Inventor: Günter Holzermer, Erlangen, Fed. Rep. of Germany

[73] Assignee: Siemens Aktiengesellschaft, Berlin & Munich, Fed. Rep. of Germany

[21] Appl. No.: 513,016

[22] Filed: Jul. 12, 1983

[30] Foreign Application Priority Data

Sep. 16, 1982 [DE] Fed. Rep. of Germany ....... 3234410

[51] Int. Cl.³ ............................................... G21F 5/04
[52] U.S. Cl. .................................. 378/152; 250/505.1
[58] Field of Search ............... 378/150, 151, 152, 153, 378/147, 148; 250/505.1

[56] References Cited

U.S. PATENT DOCUMENTS

| 2,675,486 | 4/1954 | Green et al. | 378/152 |
| 3,048,700 | 8/1962 | Koerner et al. | 378/152 |
| 4,086,494 | 4/1978 | Malak | 378/153 |
| 4,246,488 | 1/1981 | Hura | 378/151 |

FOREIGN PATENT DOCUMENTS

| 1037035 | 8/1958 | Fed. Rep. of Germany | 378/152 |
| 2053089 | 2/1980 | Fed. Rep. of Germany | 378/150 |

Primary Examiner—Alfred E. Smith
Assistant Examiner—Charles F. Wieland
Attorney, Agent, or Firm—Hill, Van Santen, Steadman & Simpson

[57] ABSTRACT

A collimator for an X-ray examination apparatus has a plurality of diaphragm plates adjustable relative to each other in pairs for defining a cone of radiation having a variable rectangular cross-section, and has a plurality of additional diaphragm plates mounted for pivotal movement into the four corner regions of the radiation cone for defining an approximately circular radiation cone of variable diameter. Each additional diaphragm plate has a substantially triangular plan shape and are movable by respective parallelogram linkages with one edge facing the radiation cone, the edge facing the radiation cone being alignable perpendicularly to the angle bisector of the respective corner in which the additional diaphragm plate is located. The additional diaphragms are respectively pivotable substantially radially in the direction of the axis of symmetry of the collimator.

9 Claims, 2 Drawing Figures

COLLIMATOR FOR AN X-RAY EXAMINATION APPARATUS

BACKGROUND OF THE INVENTION

1. Field of the Invention

The present invention relates to a collimator for an X-ray examination apparatus having several diaphragm plates adjustable in pairs relative to one another for defining a radiation cone having a rectangular cross-section of variable size, and in particular to such a collimator having an additional set of diaphragm plates pivotable at the four corner regions of the radiation cone for defining an approximately circular radiation cone of variable diameter.

2. Description of the Prior Art

A collimator for X-rays is disclosed in U.S. Pat. No. 2,675,486 wherein four diaphragm plates are mounted in a displaceable manner in a plane disposed perpendicularly to the direction of radiation propagation. This conventional collimator generates a rectangular radiation cone of variable size. If used in combination with conventional X-ray image intensifiers, which have a round inlet fluorescent screen, a 30% overshoot of radiation at the corners of the rectangular radiation cone generated by such conventional collimators is necessary in order to obtain full illumination of the field of the inlet fluorescent screen. Such radiation overshoot decreases the contrast of the resulting radiograph and increases the radiaton exposure of the patient.

Another collimator is disclosed in German As No. 1037035 for use in radiation therapy wherein four diaphragm plates are also displaceably mounted in a plane perpendicular to the direction of radiation propagation, each of the diaphragm plates being obliquely subdivided. Each diaphragm plate thus consists of two approximately triangular halves which are displaceable relative to each other by means of a spindle. This collimator which permits definition of tetragonal (square) to maximally octagonal fields, is quite costly to manufacture and moreover requires independent adjustment of five control grips in order to operate.

A collimator is described in German Pat. No. 2053089 for an X-ray examination apparatus which again has a set of diaphragm plates for defining a rectangular radiation cone and has an additional set of a diaphragm plates disposed in a different plane, those plates being triangular and having edges which slide against each other. The additional plates are adjustable along a curved guidance means about the axis of symmetry of the collimator. Depending upon the number of additional triangular diaphragm plates which are utilized, this collimator permits cross sections which approximate a circle to be defined. This collimator, however, has the disadvantage that the large number of edges of the plates sliding against each other, with substantially no gap therebetween, requires a considerable amount of friction to be overcome during adjustment. This disadvantage makes this collimator generally unsuitable for remote control. Another disadvantage is that the collimator must be regularly serviced in order to avoid jamming of the triangular diaphragm plates.

Another collimator which permits definition of a rectangular radiation cone is distributed by the Philips Company. This collimator reduces radiation overshoot of the circular inlet fluorescent screen by the use of additional diaphragm plates disposed in at least two different planes which can be pivoted into the radiation cone. The additional diaphragm plates must be arranged in at least two different planes so as to avoid obstructing each other in the case of small radiation fields. Moreover, the radiation overshoot of the round inlet fluorescent screen is dependent upon the diameter of the defined radiation cone.

SUMMARY OF THE INVENTION

It is an object of the present invention to provide a collimator for an X-ray examination apparatus which permits rectangular as well as circular radiation fields to be defined.

Another object of the present invention is to provide such a collimator wherein the radiation overshoot of a circular inlet fluorescent screen for an X-ray image intensifier is as small as possible, and is equal for all diameters of the radiation cone.

Another object of the present invention is to provide such a collimator which exhibits low friction during displacement of the diaphragm plates and is thus suitable for remote control operation.

A further object of the present invention is to provide such a collimator which occupies as small a volume as possible in the radiation direction, has a low weight, and is substantially maintenance-free.

The above objects are inventively achieved in a collimator for an X-ray examination apparatus having a set of additional diaphragm plates of substantially triangular shape which are pivotable by means of parallelogram linkages from a standby position situated laterally of the maximally definable cross-section of the radiation cone at the corners thereof, with one edge facing the cone of rays and aligned substantially perpendicularly to the angle bisector of the respective corner of the radiation cone, to a position within the radiation cone for defining the cross-sectional shape thereof. Pivoting or displacement of the respective additional diaphragm plates from the standby position into a radiation-blocking position occurs radially in the direction of the axis of symmetry of the collimator. This manner of operation and structure has the advantage that the additional diaphragm plates, in changing the shape of the radiation cone from a rectangular field to a generally circular field, do not interfer with each other even for radiating very small diameters. Because of such lack of interference between the plates, substantially no friction forces need be overcome to displace the plates. This permits all of the additional plates to be disposed in the same plane. Moreover, radiation overshoot of the circular inlet fluorescent screen for an X-ray image intensifier is independent of the diameter of the inlet fluorescent screen because of the use of parallelogram linkages for displacing the additional diaphragm plates which always maintains the same straight edge of each plate (the hypotenuse thereof) bounding the radiation cone.

The variability of the collimator can be substantially expanded in a further embodiment of the invention wherein all additional diaphragm plates are displaceable along tracks in the direction of the axis of symmetry of the collimator so that the respectively same corners of each of the plates move toward that axis of symmetry. This arrangement even further reduces the interaction between the plates disposed in the same plane even in the case of a very small radiation field. Thus randomly small approximately circular radiation fields can be defined with the same facility as larger radiation fields.

DESCRIPTION OF THE PREFERRED EMBODIMENTS

Figure 1:
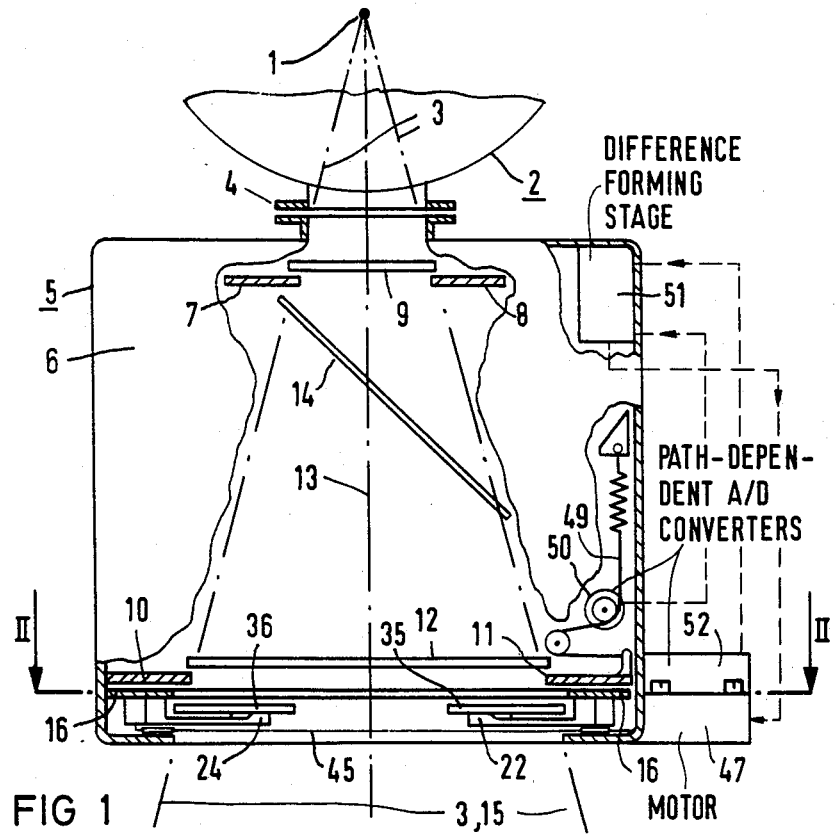
FIG. 1 is a side view, partly broken away and in section, of a collimator for an X-ray examination installation constructed in accordance with the principles of the present invention.

A collimator 5 constructed in accordance with the principles of the present invention is shown in FIG. 1 for shaping the cross-sectional area of a radiation cone 3 issuing from a focus 1 of an X-ray tube 2 having an exit flange 4. The collimator 5 has a housing 6. The radiation cone 3 is propagated into the interior of the collimator 5 wherein it is acted upon from four sides by each of four focus-proximate diaphragm plates, three of which are visible in FIG. 1 referenced at 7, 8 and 9, as well as by four focus-remote diaphragm plates, three of which are also visible in FIG. 1 referenced at 10, 11 and 12. The plates comprising the focus-remote and focus-proximate sets of diaphragm plates are respectively adjustable in pairs perpendicularly to the axis of symmetry 13 of the collimator 5 to define a rectangular radiation cone of variable size. The superimposed focus-proximate and focus-remote diaphragm plates which bound the same side of the radiation cone 3 are coupled with each other in a manner known to those skilled in the art and not further illustrated in FIG. 1. A mirror 14 is obliquely positioned in the housing 6 of the collimator 5 in the radiation cone 3 between the focus-proximate and the focus-remote diaphragm plates. A light source (not illustrated) is aligned in the housing 6 of the collimator 5 relative to the mirror 14 such that a light cone 15, reflected by the mirror 14, is defined congruently with the X-ray cone 3 by the focus-remote diaphragm plates 10, 11 and 12.

The housing 6 of the collimator 5 also has an internal frame 16 for supporting eight cantilever rods or arms 17, 18, 19, 20, 21, 22, 23 and 24 in a single plane disposed in the direction of radiation propagation immediately behind the focus-remote diaphragm plates 10, 11 and 12. The rods 17 are pivotally mounted in pairs about respective axes, 25, 26, 27, 28, 29, 30, 31 and 32 which extend parallel to the axis of symmetry 13 of the collimator 5. The rods 17 through 24 are disposed in pairs, the free ends of each pair of the arms 17 through 24 carrying a respective additional triangular diaphragm plate 33, 34, 35 or 36 pivotally mounted thereon. The two rods comprising each pair, in combination with the additional diaphragm plate mounted thereon and the internal frame 16, form a parallelogram linkage system by means of which the additional diaphragm plates 33, 34, 35 and 36 can be pivoted into the radiation cone 3 so as to block portions thereof for further defining the cross-section thereof. The additional diaphragm plates 33, 34, 35 and 36 are thus respectively pivotable, along a quarter circle curve, from a standby position at one corner of the interior frame 16 toward the axis of symmetry 13 of the collimator 5.

Alignment of the additional diaphragm plates 33, 34, 35 and 36 is selected so that each plate bounds or meets the radiation cone 3 with respective edges 37, 38, 39 and 40, which form the respective hypotenuses of the triangular plates. In the standby position, the edges 37, 38, 39 and 40 are disposed perpendicularly to the angle bisector for the respective corner of the rectangular radiation cone 3 at which the plate is located. The two other edges of each additional triangular diaphragm plate are matched to the corner region of the interior frame 16. As a consequence of the pivoting movement of the respective parallelogram system associated therewith, each of the four additional collimator plates 33, 34, 35 and 36 reaches the axis of symmetry 13 of the collimator 5 with the same respective corner. In the embodiment shown in FIG. 2, viewed from the axis of symmetry 13, this is the left corner.

Figure 2:
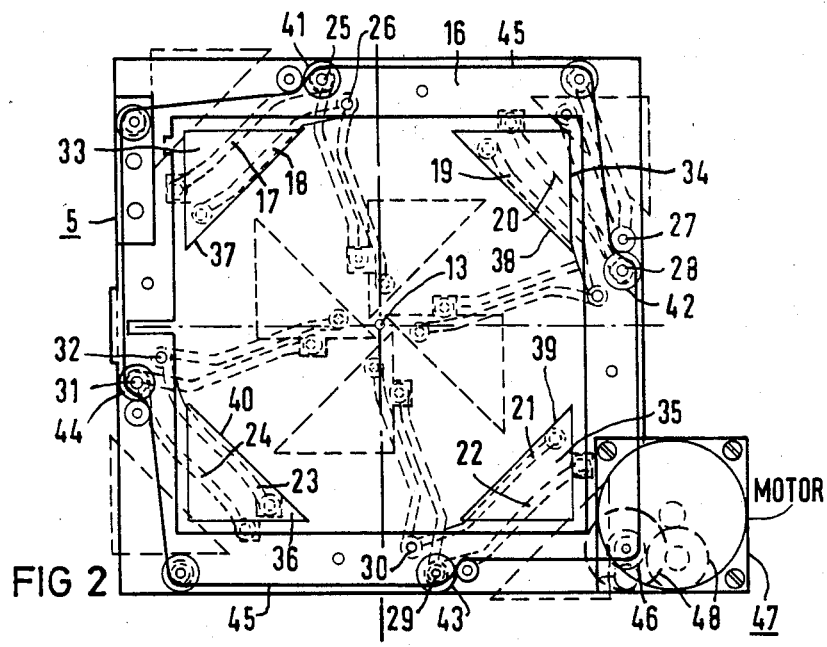
FIG. 2 is a plan view of the collimator constructed in accordance with the principles of the present invention taken along line II—II of FIG. 1.

As shown in FIGS. 1 and 2, one of the two arms in each pair of arms forming a parallelogram linkage system is coupled with respective crown gears 41, 42, 43 and 44. A continuous toothed belt 45 is trained about all four crown gears. At one corner of the interior frame 16 the continuous belt 45 is guided by a crown gear 46 which is driven by a motor 47 by means of a gear 48. One of the focus-remote plates, as shown in FIG. 1, is coupled with a spring-loaded cable line 49 by means of which a path-dependent analog-to-digital converter 50 is adjusted. The converter 50 supplies coded signals to one input of a difference-forming stage 51. The motor 47 is also coupled to a path-dependent analog-to-digital converter 52, which supplies signals to another input of the difference-forming stage 51.

During conventional fluoroscopy and radiography operations the collimator 5 may be utilized as any other collimator. The size of the radiation cone 3 is variable, in a manner known to those skilled in the art, by synchronous adjustment of the focus-proximate and focus-remote diaphragm plates 7 through 12, disposed in sequence in the direction of radiation propagation. The focus-proximate and focus-remote diaphragm plates thus define or collimate a rectangular radiation field of variable length and width. The additional diaphragm plates 33 through 36 are during this operation in the standby position indicated by the dashed lines in FIG. 2 at the extreme periphery of the interior frame 16. The plates 33 through 36 are in this position disposed beneath the interior frame 16, and protrude only a few millimeters beyond the interior corners of the frame 16, however, do not project into the radiation cone 3 maximally defined by the focus-proximate and focus-remote diaphragm plates 7 through 12. The size of the rectangular defined radiation cone 3 can thus be matched in width and length as desired to the dimensions of the examination region or to a selected cassette or film format.

If the X-ray examination apparatus is to be utilized in conjunction with an X-ray image intensifier, the size of the cone of rays is defined, by adjustment of the focus-proximate and focus-remote diaphragm plates 7 through 12 to the diameter of the inlet fluorescent screen of the image intensifier (not illustrated). In this case, however, the thus-adjusted quadratic radition field, in the region of its four corners, radiates beyond the round inlet fluorescent screen of the image intensifier. In order to reduce such radiation overshoot, the motor 47 is actuated, for example, by means of a relay (not illustrated) which responds during switch over to operation with the image intensifier. The motor 47 drives the toothed belt 45 which in turn rotates the crown gears 41 through 44 for moving the parallelogram linkages for each of the additional diaphragm plates 33 through 36 until the signals generated by the path-dependent converter 42 of the motor 47 are determined by the difference forming stage 51 to be equal to those which are supplied to the difference-forming stage 51 by the path-dependent converter 50 associated with the focus-remote diaphragm plate 11. When brought to rest, the edges 37, 38, 39 and 40 bounding the radiation cone 3 will define a radiation cone 3 which is equally as wide as that defined by the other diaphragm plates 7 through 12. The parallax difference resulting from the different focus distance of the additional diaphragm plates 33 through 36 with respect to the diaphragm plate 11 coupled to the cable line 49 is taken into account by suitable design of the gearing (or transmission) ratio in the regulating drive system.

It is also possible to adjust the additional diaphragm plates 33 through 36 with the aid of the light cone 15 cast by the mirror 14 onto the examination subject manually or with the aid of the motor 47, which may also be switched on manually. Instead of a motor having a path-dependent converter as described above, a stepping motor may be utilized, in which case a pulse counter may be employed in place of the difference-forming stage 52, the counter counting backwards by one unit with each step of a stepping motor and the motor being disconnected when the counter reaches zero.

Although other modifications and changes may be suggested by those skilled in the art it is the intention of the inventor to embody within the patent warranted hereon all changes and modifications as reasonably and properly come within the scope of his contribution to the art.

I claim as my invention:

1. A device for collimating a radiation beam comprising:
   a first diaphragm means for acting on said radiation beam for defining a radiation cone having a selected rectangular cross-section;
   a rectangular frame;
   a second diaphragm means disposed after said first diaphragm means in the direction of propagation of said radiation beam, said second diaphragm means having four triangular diaphragm plates disposed in one plane at the corners of said rectangular radiation cone, each of said triangular diaphragm plates having an edge facing said radiation cone and a prallelogram linkage means connected therewith and connected to said rectangular frame for radially pivoting said plates toward an axis of symmetry of said device parallel to said radiation propagation direction from a standby position wherein said edges of said plates are respectively disposed substantially perpendicularly to each angle bisector of the corners of said frame and wherein said plates substantially do not act on said radiation cone, to selected central positions for defining a substantially circular radiation cone of selected diameter; and
   a means for driving said parallelogram linkage means.

2. A device as claimed in claim 1 wherein each of said triangular diaphragm plates has a corner when viewed from said axis of symmetry which follow respective paths becoming increasingly closer to said axis of symmetry as said plates are pivoted.

3. A device as claimed in claim 1 wherein said means for driving said parallelogram linkage means includes a common regulating means for synchronously driving all of said parallelogram linkage means.

4. A device as claimed in claim 3 wherein each of said parallelogram linkage means has at least one arm and wherein said common regulator includes at least four crown gears respectively conected to said one arm in each of said prallelogram linkage means and a toothed belt trained about all of said crown gears and connected to said drive means for rotating said crown gears.

5. A device as claimed in claim 4 wherein said drive means is a motor.

6. A device as claimed in claim 5 wherein said first diaphragm means includes at least one pair of first diaphragm means plates and further comprising a means connecting said drive means to said pair of first diaphragm plates for displacement thereof and a path-dependent monitoring means for measuring the amount of displacement of said pair of first diaphragm means plates and control circuitry connected to said monitoring means and to said motor for controlling said motor for effecting a selected displacement of said pair of first diaphragm means plates.

7. A device as claimed in claim 6 further comprising a path-dependent monitoring means connected to said motor for monitoring displacement of said triangular diaphragm plates and wherein said control circuitry is a difference-forming stage for comparing the displacement of said triangular diaphragm plates and the displacement of said pair of first diaphragm means plates and for controlling said motor in dependence upon said comparison.

8. A device as claimed in claim 5 wherein said drive means is a stepping motor.

9. A collimator for an X-ray examination apparatus for collimating a beam of X-rays comprising:
   a first diaphragm means including oppositely disposed displaceable pairs of diaphragm plates for acting on said beam for defining a radiation cone having a selected rectangular cross-section;
   a rectangular frame in said collimator;
   a second diaphragm means disposed after said first diaphragm means in the direction of propagation of said radiation beam, said second diaphragm means having four triangular diaphragm plates disposed in one plane at the corners of said rectangular radiation cone, each of said triangular diaphragm plates having an edge facing said radiation cone and a parallelogram linkage means connected to each of said triangular diaphragm plates and to said rectangular frame for radially pivoting said plates toward and axis of symmetry of said device which is parallel to said radiaton propagation direction from a standby position wherein said edges of said plates are respectively disposed substantially perpendicularly to each angle bisector of the corners of said frame and wherein said plates substantially do not act on said radiaton cone, to selected central positions for defining a substantially circular radiation cone of selected diameter; and
   a means for driving said parallelogram linkage means for pivoting said plates.

* * * * *